(12) United States Patent
Schleich (10) Patent No.: US 8,285,385 B2
(45) Date of Patent: Oct. 9, 2012

(54) HIGH ACCURACY TONOTOPIC AND PERIODIC CODING WITH ENHANCED HARMONIC RESOLUTION

(75) Inventor: Peter Schleich, Vill (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 351 days.

(21) Appl. No.: 12/690,486

(22) Filed: Jan. 20, 2010

(65) Prior Publication Data

US 2010/0185261 A1 Jul. 22, 2010

Related U.S. Application Data

(60) Provisional application No. 61/145,805, filed on Jan. 20, 2009.

(51) Int. Cl.
*A61N 1/18* (2006.01)
(52) U.S. Cl. ........................................... 607/57
(58) Field of Classification Search .............. 607/55–57
See application file for complete search history.

(56) References Cited

U.S. PATENT DOCUMENTS

| | | | |
|---|---|---|---|
| 4,515,158 A | 5/1985 | Patrick et al. | 128/419 R |
| 5,434,924 A | 7/1995 | Jampolsky | 381/68.4 |
| 6,584,525 B1 | 6/2003 | Klingman | 701/118 |
| 6,778,858 B1 | 8/2004 | Peeters | 607/57 |
| 7,072,717 B1 | 7/2006 | Wolf et al. | 607/57 |
| 7,104,417 B2 | 9/2006 | Hilliard | 221/25 |
| 7,149,583 B1 | 12/2006 | Litvak | 607/57 |
| 7,209,789 B2 | 4/2007 | Zierhofer | 607/57 |
| 7,225,027 B2 | 5/2007 | Zeng | 607/57 |
| 7,251,530 B1 | 7/2007 | Overstreet et al. | 607/55 |
| 7,292,892 B2 | 11/2007 | Litvak et al. | 607/57 |
| 7,310,558 B2 | 12/2007 | Van Hoesel | 607/57 |

(Continued)

FOREIGN PATENT DOCUMENTS

EP 1338301 A1 8/2003

(Continued)

OTHER PUBLICATIONS

McKay, Collette, et al., "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

(Continued)

*Primary Examiner* — Scott Getzow
*Assistant Examiner* — Amanda Patton
(74) *Attorney, Agent, or Firm* — Sunstein Kann Murphy & Timbers LLP (57) ABSTRACT

Generating electrode stimulation signals for an implanted electrode array is described. An acoustic audio signal is processed to generate band pass signals which represent associated bands of audio frequencies. Macro bands are defined, each of which characterizes multiple band pass signals. The macro bands are processed in a sequence of sampling intervals. For each sampling interval, the processing includes: i. extracting timing and energy information from each band pass signal to form requested stimulation events, ii. decimating the requested stimulation events to select a maximum energy band pass signal within each macro band, and iii. decimating each selected band pass signal based on a pulse selection inhibition function and preserving temporal and spectral structures of the band pass signals so as to generate stimulation event signals. The stimulation event signals are weighted with a weighting matrix reflecting patient-specific pitch perception characteristics to produce output electrode stimulation signals to the implanted electrode array.

18 Claims, 8 Drawing Sheets

U.S. PATENT DOCUMENTS

| | | |
|---|---|---|
| 7,421,298 B2 | 9/2008 | Daly et al. ............. 607/57 |
| 7,627,379 B2 | 12/2009 | Kitazawa et al. ............. 607/57 |
| 2001/0031909 A1 | 10/2001 | Faltys et al. ............. 600/25 |
| 2004/0082985 A1 | 4/2004 | Faltys et al. ............. 607/116 |
| 2005/0107843 A1 | 5/2005 | McDermott et al. ............. 607/57 |
| 2005/0203589 A1 | 9/2005 | Zierhofer ............. 607/57 |
| 2006/0052841 A1 | 3/2006 | Daly et al. ............. 607/57 |
| 2006/0100672 A1 | 5/2006 | Litvak ............. 607/57 |
| 2006/0265061 A1 | 11/2006 | Kwon et al. ............. 623/10 |
| 2007/0156202 A1 | 7/2007 | Zierhofer ............. 607/57 |
| 2007/0225776 A1 | 9/2007 | Fritsch et al. ............. 607/57 |
| 2008/0172108 A1 | 7/2008 | Zierhofer et al. ............. 607/57 |
| 2009/0012580 A1 | 1/2009 | Arnoldner et al. ............. 607/57 |
| 2010/0198300 A1 | 8/2010 | Smith ............. 607/57 |
| 2010/0198301 A1 | 8/2010 | Smith ............. 607/57 |

FOREIGN PATENT DOCUMENTS

| | | |
|---|---|---|
| WO | WO 99/49815 | 10/1999 |
| WO | WO 01/19135 A1 | 3/2001 |
| WO | WO 01/19304 A1 | 3/2001 |
| WO | WO 2005/113064 A | 12/2005 |
| WO | WO 2006/119069 | 11/2006 |

OTHER PUBLICATIONS

Secker-Walker, H., et al., "Time-domain analysis of auditory-nerve-fiber firing rates", *J. Acoust. Soc. Am.* 88(3), pp. 1427-1436 (1990).

Wilson, B.S., et al., "Temporal Representations with Cochlear Implants", *Am. J. Otology*, vol. 18, No. 6 (Suppl), S30-S34, (1997).

Wilson, B.S., et al., "Comparative Studies of Speech Processing Strategies for Cochlear Implants", *Laryngoscope* (1998); pp. 1069-1077.

Zeng, F., et al., "Cochlear Implants: System Design, Integration, and Evaluation", *IEEE Reviews in Biomedical Engineering*, vol. 1, 2008, pp. 115-142.

Ziese, M., et al., "Speech Understanding with the CIS and the n-of-m Strategy in the MED-EL COMBI 40+ System", *ORL* 2000:62:321-329.

European Patent Office, International Search Report dated Nov. 16, 2005, PCT/IB2005/002349.

European Patent Office, International Search Report dated Jan. 27, 2009, PCT/US2008/079923.

European Patent Office, International Search Report dated Sep. 3, 2009, PCT/IB2009/005813.

HIGH ACCURACY TONOTOPIC AND PERIODIC CODING WITH ENHANCED HARMONIC RESOLUTION

This application claims priority from U.S. Provisional Patent Application 61/145,805, filed Jan. 20, 2009, incorporated herein by reference.

FIELD OF THE INVENTION

The present invention relates to implantable medical devices, and more specifically, to techniques for coding stimulation pulses in such devices, for example, cochlear implant systems.

BACKGROUND ART

Cochlear implants can provide hearing to profoundly deaf or severely hearing impaired persons. Unlike conventional hearing aids which mechanically apply an amplified sound signal to the middle ear, a cochlear implant provides direct electrical stimulation to multiple stimulation electrodes that excite the acoustic nerve in the inner ear. Most existing cochlear implant stimulation coding strategies represent a sound signal by splitting it into distinct frequency bands and extracting the envelope (i.e., energy) of each of these bands. These envelope representations of the acoustic signal are used to define the pulse amplitude of stimulation pulses to each electrode.

The number of band pass signals typically equals the number of stimulation electrodes, and relatively broad frequency bands are needed to cover the acoustic frequency range. A typical acoustic signal such as a human voice producing a vowel includes a fundamental frequency and additional harmonics that are multiples of the fundamental frequency. So if the fundamental frequency is typically between 100 and 200 Hz, then there will also be frequency harmonics that are spaced every 100 to 200 Hz. In existing cochlear implant systems, the band pass filter band widths are usually more than 100 Hz, so that more than one harmonic is usually processed by each band pass filter.

In modern fine structure coding strategies, the stimulation signal timing is derived from the filter bank band pass signals. When multiple harmonics fall within a given frequency band, the derived stimulation timing is usually not representative of any particular harmonic but instead depends on the relative amplitudes and frequency spacing. This means that the stimulation timing in low-to-mid frequency channels is relatively complex instead of simply coding the periodicity of the dominant harmonics. Usually one specific harmonic dominates a filter band, and in normal hearing such a dominant harmonic masks the neighboring harmonics and carries the audio information that should be tonotopically and temporally correct.

In psychoacoustic pitch testing, both periodic pitch and tonotopic pitch concepts have been demonstrated to work for cochlear implant patients. A gradual shift of the stimulation pattern from an apical electrode towards a more basal one at relatively high rates leads to an increase in pitch percept. Nobbe et al. (Acta Oto-Laryngologica, 2007; 127: 1266-1272; incorporated herein by reference) showed that either simultaneous or sequential stimulation leads to just noticeable differences in pitch changes of down to one semitone. Similar results can be found if the low stimulation rate of one electrode is increased, in which case, just noticeable differences in pitch range to within one semitone. These results suggest that a combination of both types of pitch cues could lead to better pitch perception in cochlear implant users. But in existing cochlear implant systems, both tonotopic and periodic pitch cues are not integrated at the same time. The temporal fine structure of the input signal is analyzed in relatively broad bands, and this generates shifts in stimulation patterns at transitions between analysis filters which can lead to unexpected and unwanted changes in pitch percepts.

One coding strategy that partially addresses the above is the Fine Structure Processing (FSP) strategy used in the Med-El OPUS 1 and OPUS 2 speech processors. The FSP strategy codes very low frequency harmonics, usually the fundamental frequency and the second harmonic, by using a filter bank that ranges down to below the expected fundamental frequencies. The spacing of the lowest frequency bands is such that the harmonics coded are usually resolved, that is, only one harmonic falls into one low frequency filter band. But higher harmonics are not explicitly resolved by this type of signal processing. In addition, the shift of harmonics is mainly coded temporally. A tonotopic shift of the temporal code of fundamental frequency gliding from 100 Hz up is only achieved at around 200 Hz.

The HiRes 120 strategy of Advanced Bionics Corporation uses active current steering and additional spectral bands. The input signal is filtered into a large number of spectral bands and a fast Fourier transformation (FFT) algorithm is applied for fine spectral resolution. Hilbert processing derives temporal detail from the signals while the spectral maximum for each electrode pair is determined across all the filter bands. Pulse rate and stimulus location are determined from the estimated frequency of the spectral maximum. A number of spectral bands are assigned to each electrode pair and the spectral bands are delivered to locations along the electrode array by varying the proportion of current delivered simultaneously to adjacent electrodes in each electrode pair.

SUMMARY OF THE INVENTION

Embodiments of the present invention are directed to generating electrode stimulation signals for an implanted electrode array such as for a cochlear implant system. An acoustic audio signal is processed to generate band pass signals which represent associated bands of audio frequencies. Macro bands are defined, each of which characterizes multiple band pass signals. The macro bands are processed in a sequence of sampling intervals. For each sampling interval, the processing includes: i. extracting timing and energy information from each band pass signal to form requested stimulation events, ii. decimating the requested stimulation events to select a maximum energy band pass signal within each macro band, and iii. decimating each selected band pass signal based on a pulse selection inhibition function and preserving temporal and spectral structures of the band pass signals so as to generate stimulation event signals. The stimulation event signals are weighted with a weighting matrix reflecting patient-specific pitch perception characteristics to produce output electrode stimulation signals to the implanted electrode array.

Decimating each selected band pass signal may also take into account spatial channel interaction characteristics and/or target nerve refractory properties. Zero crossings or phase of the band pass signals may be used for extracting timing and energy information from each band pass signal. Channel specific sampling sequences (CSSS) may be used to code timing and energy information. The maximum energy band pass signal may be selected based on signal envelopes of the band pass signals. The number of band signals may be much greater than the number of electrode stimulation signals. The electrode stimulation signals may include simultaneous electrode stimulation signals.

Embodiments of the present invention also include a computer program product implemented in a computer readable storage medium for generating electrode stimulation signals for an implanted electrode array according to any of the above. Embodiments also include a cochlear implant system operating according to any of the above.

DETAILED DESCRIPTION OF SPECIFIC EMBODIMENTS

Embodiments of the present invention are directed to generating electrode stimulation signals for an implanted electrode array for a cochlear implant system which preserves temporal and spectral characteristics of the original audio input signal. A high accuracy technique codes tonotopic and periodic pitch information with enhanced harmonic resolution. This provides enhanced temporal coding of dominant signal components such as formants and low frequency harmonics.

Figure 1:
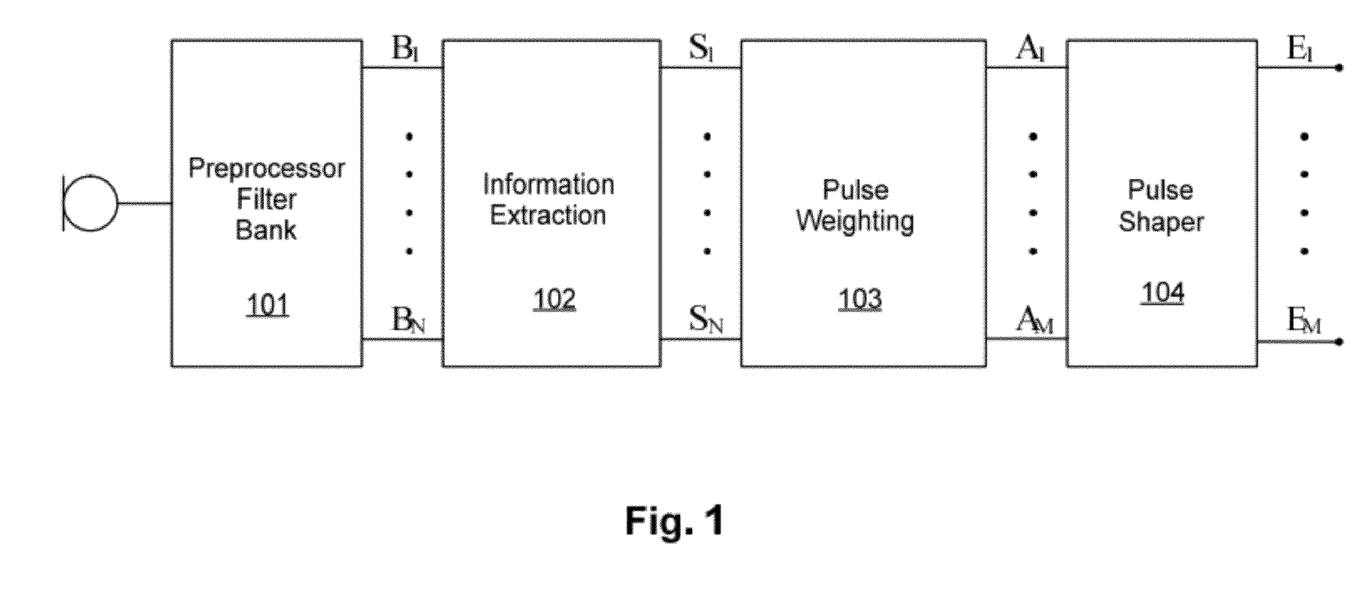
FIG. 1 shows functional signal processing blocks according to an embodiment of the present invention.

FIG. 1 shows various functional signal processing blocks according to one specific embodiment of the present invention wherein N band pass signals containing stimulation timing and amplitude information are assigned to M stimulation electrodes. Preprocessor Filter Bank 101 pre-processes an initial acoustic audio signal, e.g., automatic gain control, noise reduction, etc. Each band pass filter in the Preprocessor Filter Bank 101 is associated with a specific band of audio frequencies so that the acoustic audio signal is filtered into some N band pass signals, $B_1$ to $B_N$ where each signal corresponds to the band of frequencies for one of the band pass filters.

The band pass signals are input to an Information Extractor 102 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference. The band pass signals are pooled into a smaller number of overlapping macro bands, and within each macro band the channel with the highest envelope is selected for a given sampling interval. The stimulation events are decimated based on channel interaction and inhibition functions.

Pulse Weighting 103 weights each requested stimulation event signal $S_1$ to $S_N$ with a weighted matrix of M stimulation amplitudes that reflect patient-specific perceptual characteristics to produce a set of electrode stimulation signals $A_1$ to $A_M$ that provide and optimal electric tonotopic representation of the acoustic signal. Matrix weighting of the stimulation pulses is described further in U.S. Patent Application 61/046,832, filed Apr. 22, 2008, which is incorporated herein by reference. Equation 1 shows a typical weighting matrix of size M×N:

$$W = \begin{pmatrix} 1 & 0.923 & 0.846 & \ldots & \ldots & 0 & 0 & 0 \\ 0 & 0.077 & 0.154 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.154 & 0.077 & 0 \\ 0 & 0 & 0 & \ldots & \ldots & 0.846 & 0.923 & 1 \end{pmatrix} \quad \text{Equation 1}$$

Finally, patient specific stimulation is achieved by individual amplitude mapping and pulse shape definition in Pulse Shaper 104 which develops the set of electrode stimulation signals $A_1$ to $A_M$ into a set of output electrode pulses $E_1$ to $E_M$ to the electrodes in the implanted electrode array which stimulate the adjacent nerve tissue. Whenever one of the requested stimulation event signals $S_1$ to $S_N$ requests a stimulation event, the respective number of electrodes is activated with a set of output electrode pulses $E_1$ to $E_M$.

Figure 2:
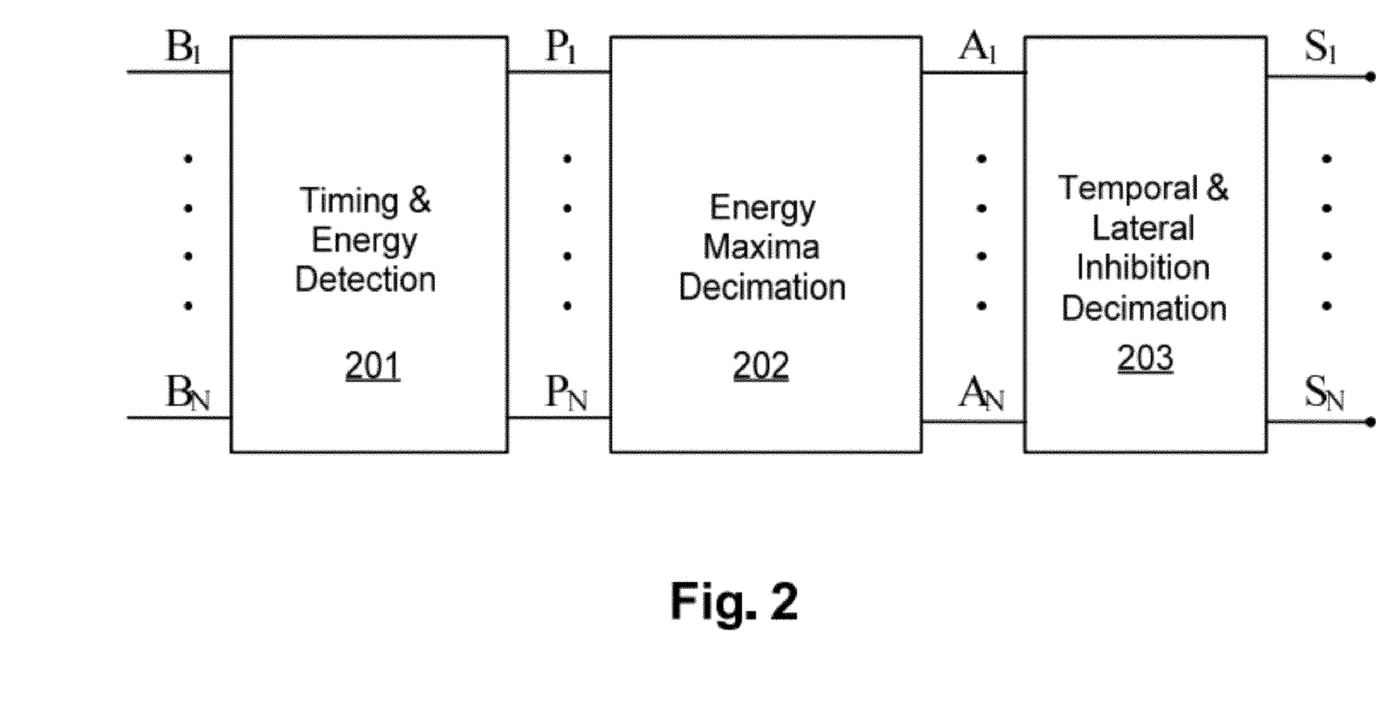
FIG. 2 shows functional blocks in the information extraction (IE) stage of one specific embodiment.
Figure 3:
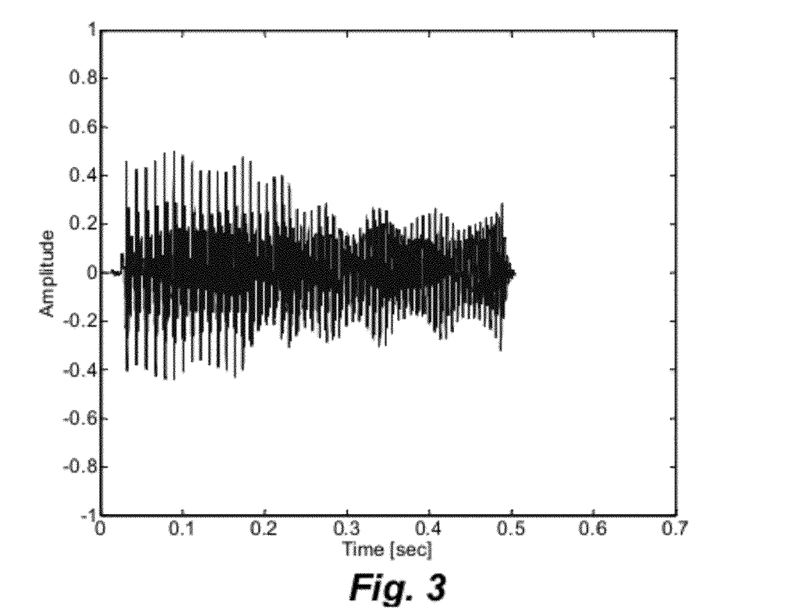
FIG. 3 shows an example of a typical acoustic signal, a vowel glide.
Figure 4:
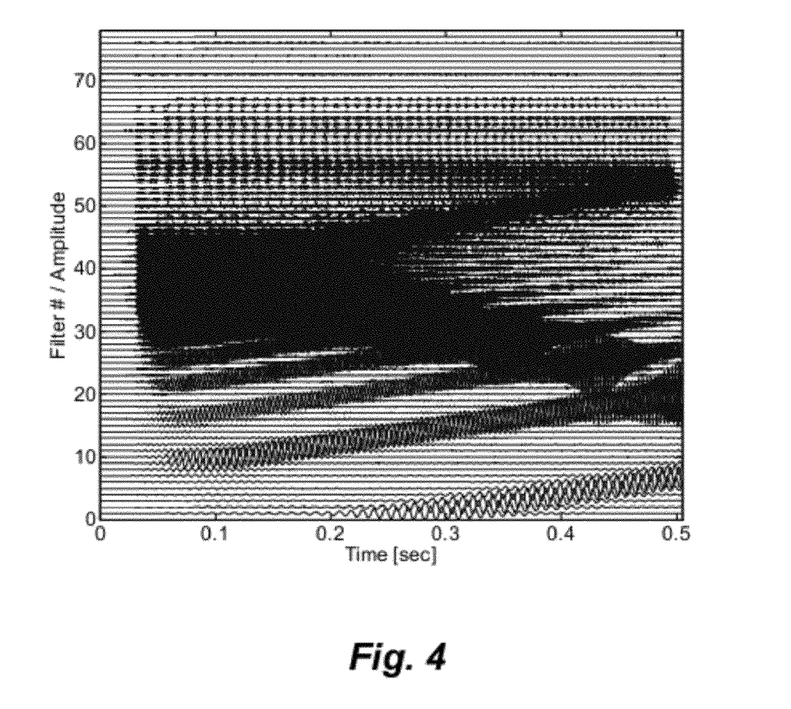
FIG. 4 shows an example of an acoustic signal decomposed into a set of 77 separate frequency band signals.
Figure 5:
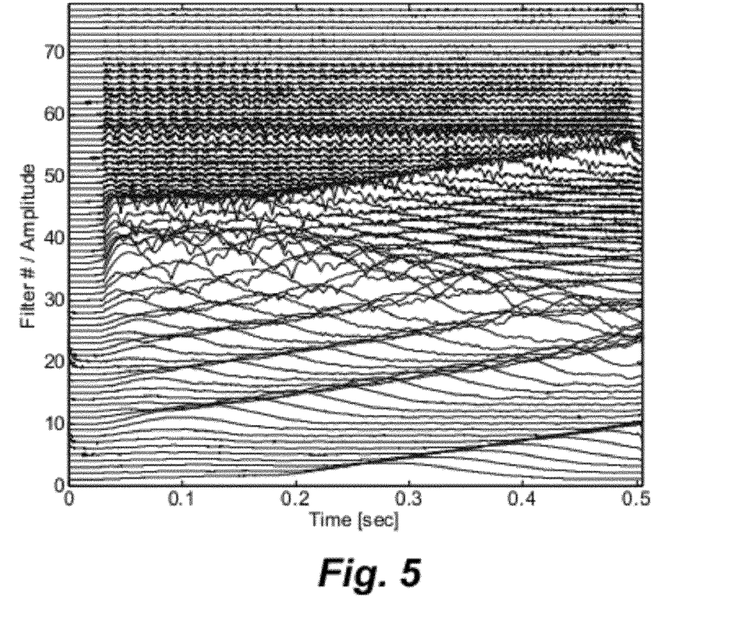
FIG. 5 shows examples of the band pass signal envelopes.
Figure 6:
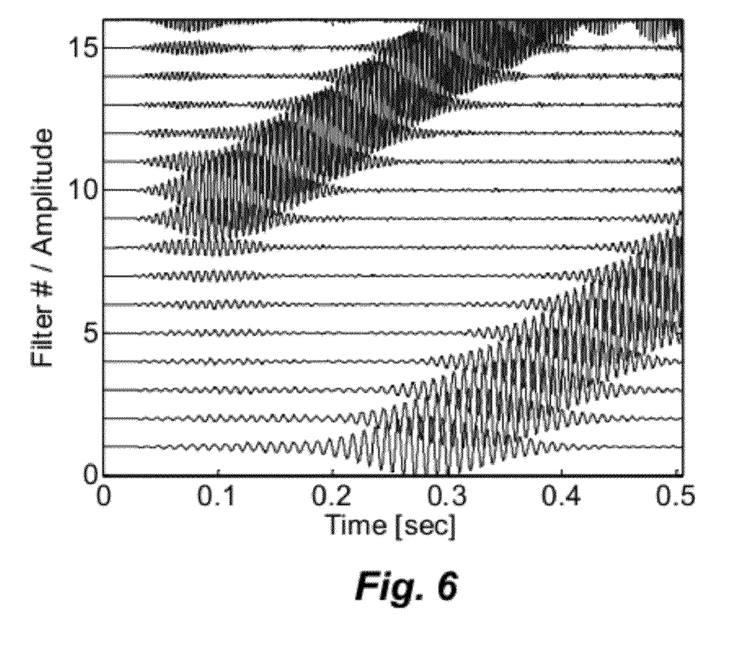
FIG. 6 shows details of the lowest 15 band pass signals.
Figure 7:
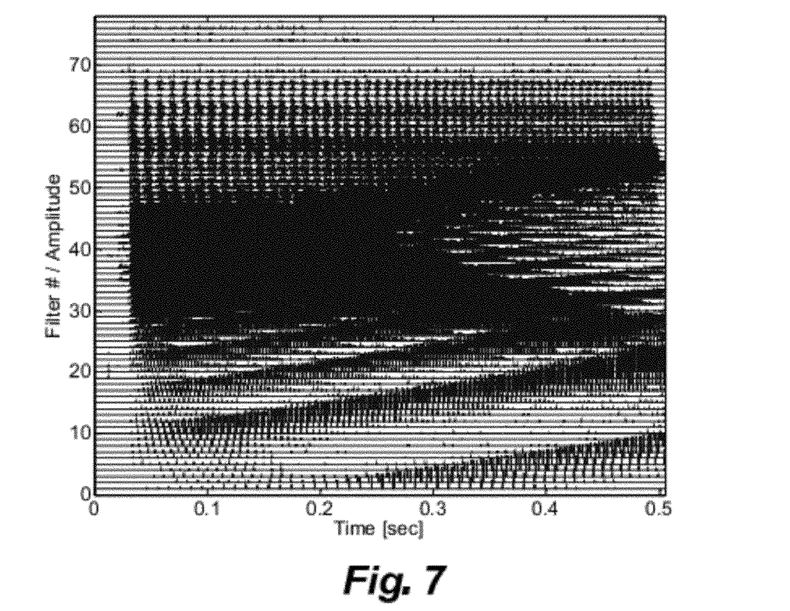
FIG. 7 shows an example of the requested stimulation events.

FIG. 2 is a functional block diagram showing further detail regarding the information extraction within the information extractor 102. Timing and Energy Detection 201 derives timing and energy information within each band pass signal, e.g. zero crossings or the phase of the band pass signal. The envelope of the band pass signal is typically determined such as by using a Hilbert transform or by rectification and low-pass filtering. FIG. 3 depicts a typical voice signal in the specific form of a synthetic vowel glide, which contains a rising fundamental frequency and corresponding rising harmonics, as well as one falling and one rising formant. FIG. 4 shows the band pass signals $B_1$-$B_N$ produced by the Preprocessor Filter Bank 101 for this input signal, and FIG. 5 shows the envelope signals derived from the band pass signals $B_1$-$B_N$ using a Hilbert transform. FIGS. 4 and 5 both reflect various characteristic properties of the synthetic vowel such as a rising fundamental frequency seen in a shift of the maximum envelope from filter band signal #1 to #7, as well as an increase of signal frequency within the excited bands. FIG. 6 shows an increasing voice fundamental frequency and second harmonic in frequency bands 1 to 15. FIG. 7 shows all the requested stimulation time events (i.e. requested stimulation pulses) calculated from $B_1$-$B_N$ by the Timing and Energy Detection 201 stage. Temporal and spectral characteristics are well preserved up to this stage of signal processing.

The Energy Maxima Decimation 202 block reduces the large number of requested stimulation events based on the energy in the filter bands, which are pooled together into a smaller number of macro band groups. For each sampling interval within each macro band the channel with the maximum amplitude is determined and only requested stimulation events within the selected filter bands are used for further processing. Channel selection is further described in U.S. Pat.

Figure 8:
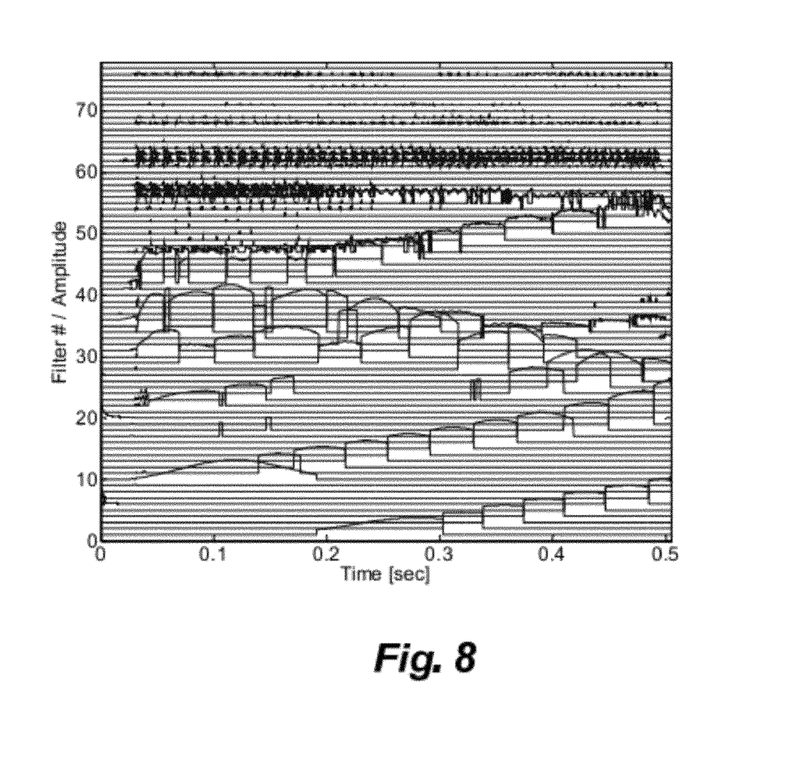
FIG. 8 shows selected envelopes of the band pass signals within the second stage of the information extraction module.

No. 7,283,876, which is incorporated herein by reference. FIG. 8 shows examples of the envelopes of the selected band pass signals within Energy Maxima Decimation 202 block.

Figure 9:
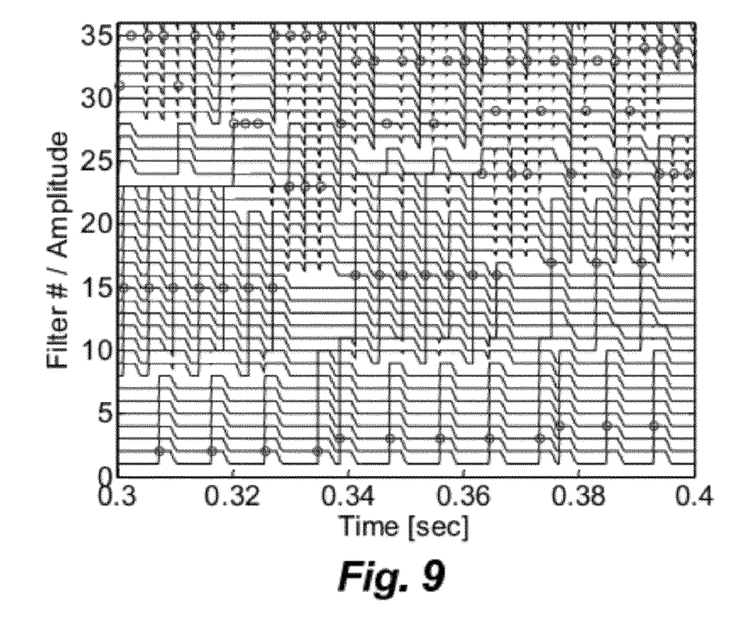
FIG. 9 shows examples of the inhibition states of the filters.
Figure 10:
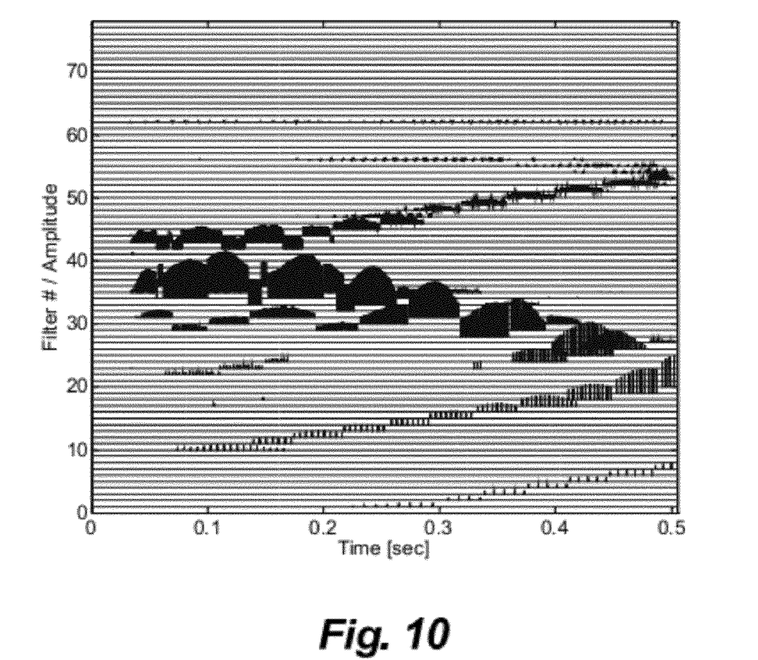
FIG. 10 shows examples of selected stimulation events within selected bands.
Figure 11:
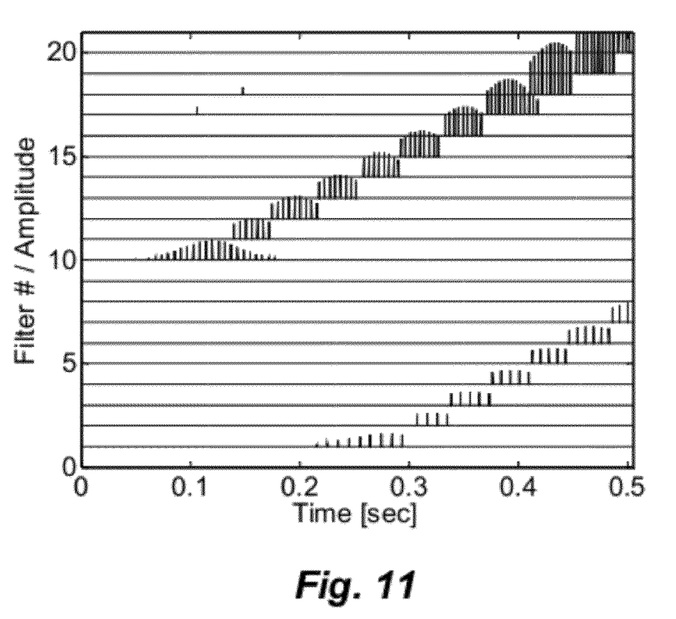
FIG. 11 shows examples of selected stimulation events on channels 1 to 20.

The Temporal & Lateral Inhibition Decimation 203 block defines an inhibition state for each channel as described further in U.S. patent application Ser. No. 12/267,858, filed Nov. 10, 2008, which is incorporated herein by reference. In this stage, the stimulation pulses are further reduced using a model of refractory properties of the acoustic nerve. Channel inhibition can also be applied to neighboring channels. FIG. 9 shows examples of the inhibition state of each selected band pass signal, where upward shifts of the inhibited regions around the selected low frequency harmonics can be clearly identified. After a stimulation event is selected on a specific channel, the inhibition state of the selected channel that of neighboring channels is reset. The resulting selected stimulation events are depicted in FIG. 10. Although the number of stimulation events has been drastically reduced in this processing stage, the dominant temporal and spectral structures of the original signal are still preserved which can be clearly observed in low frequency bands shown in FIG. 11.

Figure 12:
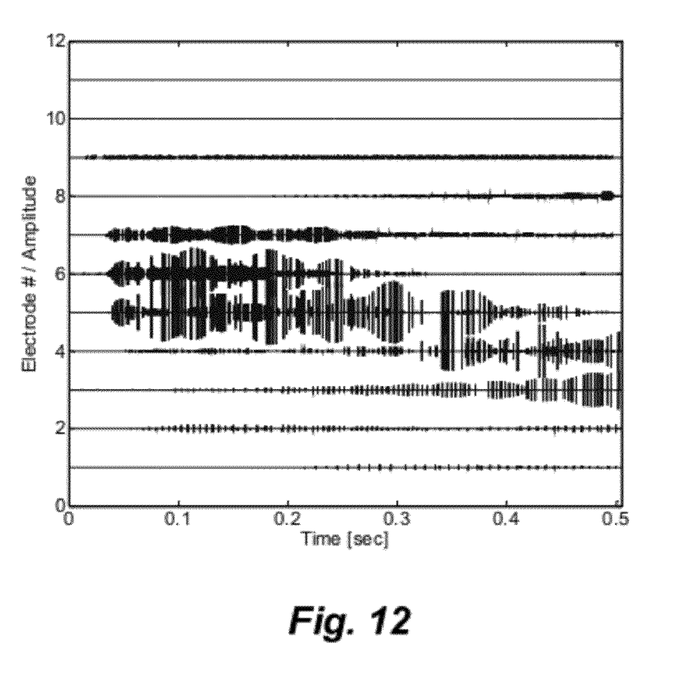
FIG. 12 shows simultaneous stimulation of requested pulses mapped to a smaller number of electrodes.
Figure 13:
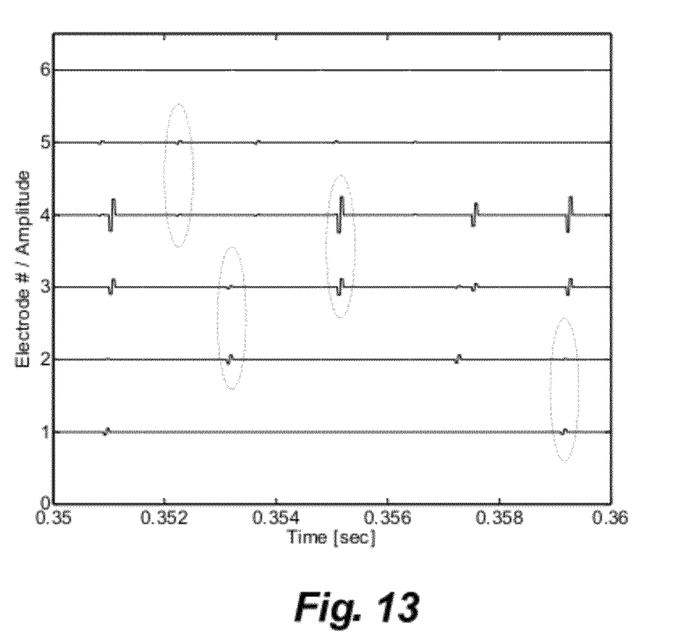
FIG. 13 shows details of simultaneous stimulation.
Figure 14:
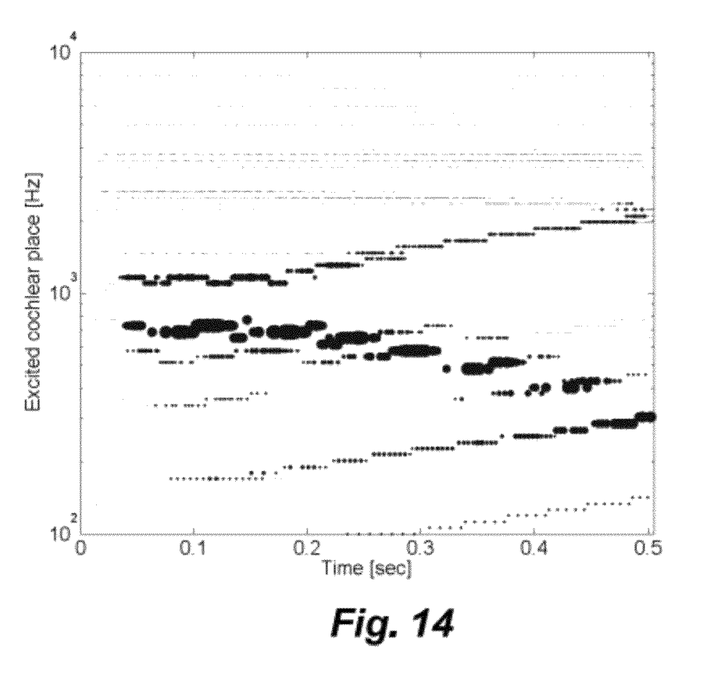
FIG. 14 shows examples of excitation maxima along the cochlea.

FIG. 12 shows simultaneous stimulation pulses as produced after weighting of each selected band pass channel and patient specific amplitude mapping, which can be applied to the stimulation electrodes in the implanted electrode array. FIG. 13 shows in detail the simultaneous simulation of two adjacent electrode pairs. For each sampling interval, the modeled corresponding frequency of maximum excitation was calculated and is shown in FIG. 14. This analysis shows that the tonotopic and periodic structure of the original signal is transmitted by a specific embodiment of the described invention.

An embodiment of the present invention as described above provides enhanced temporal coding of dominant signal components such as formants and low frequency harmonics. There is also an improved match between tonotopicity and periodicity of cochlear implant stimulation. In addition, the input audio signal is analyzed with more filter bands than in the prior art. As a result, there can be improved representation of musical signals, for example, using a semitone-filter bank. Because there are so many filter bands, each band is much more narrow, which enables the dominant signal components (usually harmonics) to be identified. The timing of the requested stimulation pulses is directly derived from the selected band pass signal, and within each macro band, just one band pass signal is selected, which usually encodes a dominant harmonic. Thus only dominant harmonics are coded and easily tracked, and interactions of unresolved harmonics with the derived stimulation timing are greatly reduced.

With a cochlear implant system that, for example, assigns a total of 77 analysis filters to 12 stimulation contacts, the limit of temporal interactions between harmonics can be pushed far beyond the relevant formant frequencies of speech signals. Especially for low frequency harmonics, a large number of analysis filter bands certainly leads to more gradual and natural shift of pitch percept if the frequency of the signal increases gradually. In current cochlear implant systems, a gradual shift of signal frequency often produces masking of stimulation pulses requested from adjacent filter bands. This effect can be avoided in specific embodiments of the present invention. In addition, the large number of analysis filter bands and the weighted assignment to the stimulation contacts allows accurate fitting of the system. The weighting matrix can be manipulated so that musical intervals are perceived correctly by the cochlear implant user. And neuron refractory properties and channel cross talk can be taken into account when reducing the number of simultaneous stimulation events. Thus the system increases temporal accuracy by ensuring that only unmasked stimulation pulses are applied.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as preprogrammed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array, the method comprising:

processing an acoustic audio signal to generate a plurality of band pass signals, each of which represents an associated band of audio frequencies;

defining a plurality of macro bands, each of which characterizes a plurality of the band pass signals;

processing the macro bands in a sequence of sampling intervals, wherein for each sampling interval the processing includes:

i. extracting timing and energy information from each band pass signal to form requested stimulation events, ii. decimating the requested stimulation events to select a maximum energy band pass signal within each macro band, and iii. decimating each selected band pass signal based on a pulse selection inhibition function and preserving temporal and spectral structures of the band pass signals so as to generate stimulation event signals; and
weighting the stimulation event signals with a weighting matrix reflecting patient-specific pitch perception characteristics to produce output electrode stimulation signals to the implanted electrode array.

2. A method according to claim 1, wherein decimating each selected band pass signal also takes into account spatial channel interaction characteristics.

3. A method according to claim 1, wherein decimating each selected band pass signal also takes into account target nerve refractory properties.

4. A method according to claim 1 wherein zero crossings of the band pass signals are used for extracting timing and energy information from each band pass signal.

5. A method according to claim 1 wherein the phase of the band pass signals are used for extracting timing and energy information from each band pass signal.

6. A method according to claim 1, wherein channel specific sampling sequences (CSSS) is used for extracting the coding timing and energy information.

7. A method according to claim 1, wherein the maximum energy band pass signal is selected based on signal envelopes of the band pass signals.

8. A method according to claim 1, wherein the number of band signals is greater than the number of electrode stimulation signals.

9. A method according to claim 1, wherein the electrode stimulation signals include simultaneous electrode stimulation signals.

10. A computer program product implemented in a computer readable storage medium for generating electrode stimulation signals for an implanted electrode array, the product comprising:
   program code for processing an acoustic audio signal to generate a plurality of band pass signals, each of which represents an associated band of audio frequencies;
   program code for defining a plurality of macro bands, each of which characterizes a plurality of the band pass signals;
   program code for processing the macro bands in a sequence of sampling intervals, wherein for each sampling interval the processing includes:
   i. extracting timing and energy information from each band pass signal to form requested stimulation events,
   ii. decimating the requested stimulation events to select a maximum energy band pass signal within each macro band, and
   iii. decimating each selected band pass signal based on a pulse selection inhibition function and preserving temporal and spectral structures of the band pass signals so as to generate stimulation event signals; and
   program code for weighting the stimulation event signals with a weighting matrix reflecting patient-specific pitch perception characteristics to produce output electrode stimulation signals to the implanted electrode array.

11. A product according to claim 10, wherein decimating each selected band pass signal also takes into account spatial channel interaction characteristics.

12. A product according to claim 10, wherein decimating each selected band pass signal also takes into account target nerve refractory properties.

13. A product according to claim 10 wherein zero crossings of the band pass signals are used for extracting timing and energy information from each band pass signal.

14. A product according to claim 10 wherein phase of the band pass signals are used for extracting timing and energy information from each band pass signal.

15. A product according to claim 10, wherein channel specific sampling sequences (CSSS) is used for extracting the coding timing and energy information.

16. A product according to claim 10, wherein the maximum energy band pass signal is selected based on signal envelopes of the band pass signals.

17. A product according to claim 10, wherein the number of band signals is greater than the number of electrode stimulation signals.

18. A product according to claim 10, wherein the electrode stimulation signals include simultaneous electrode stimulation signals.

* * * * *